(12) United States Patent
Bechini

(10) Patent No.: US 7,811,533 B2
(45) Date of Patent: *Oct. 12, 2010

(54) UNIT FOR STERILISING AND DEPYROGENATING CONTAINERS

(75) Inventor: Claudio Bechini, Castelnuovo Berardenga (IT)

(73) Assignee: I.M.A. Industria Macchine Automatiche S.p.A., Ozzano Dell'Emilia (BO) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 11/794,656

(22) PCT Filed: Jan. 11, 2006

(86) PCT No.: PCT/IB2006/000029

§ 371 (c)(1),
(2), (4) Date: Mar. 3, 2008

(87) PCT Pub. No.: WO2006/075227

PCT Pub. Date: Jul. 20, 2006

(65) Prior Publication Data

US 2008/0260609 A1 Oct. 23, 2008

(30) Foreign Application Priority Data

Jan. 12, 2005 (IT) .......................... BO2005A0011

(51) Int. Cl.
*A61L 2/04* (2006.01)

(52) U.S. Cl. ..................................... 422/308; 414/150
(58) Field of Classification Search ................. 414/150; 422/308

See application file for complete search history.

(56) References Cited

U.S. PATENT DOCUMENTS

| 4,962,700 | A | 10/1990 | Ivo et al. | |
|---|---|---|---|---|
| 6,436,343 | B1 * | 8/2002 | Bechini | ....................... 422/28 |
| 7,581,367 | B2 * | 9/2009 | Bechini | .................... 53/111 R |
| 2004/0105798 | A1 * | 6/2004 | Windsheimer | .............. 422/308 |

FOREIGN PATENT DOCUMENTS

| EP | 0 992 246 | 4/2000 |
|---|---|---|
| WO | 98/48854 | 11/1998 |

OTHER PUBLICATIONS

International Search Report mailed Feb. 20, 2002.

* cited by examiner

*Primary Examiner*—Elizabeth L McKane
(74) *Attorney, Agent, or Firm*—Nixon & Vanderhye P.C.

(57) ABSTRACT

A unit for sterilizing and depyrogenating containers of the type including a conveying device suitable for receiving a plurality of containers through at least an inlet and supplying the containers in a set direction to a corresponding outlet of the unit. The unit has a sterilizing/depyrogenating unit defined by at least two sterilizing modules arranged consecutively in said direction and communicating through an intermediate passage and affected by the conveying device. The sterilizing modules are activatable independently of one another according to alternative operating modes for hot and/ or cooling sterilizing the containers.

6 Claims, 2 Drawing Sheets

UNIT FOR STERILISING AND DEPYROGENATING CONTAINERS

This application is the U.S. national phase of International Application No. PCT/IB2006/000029 filed 11 Jan. 2006 which designated the U.S. and claims priority to IT BO2005A000011 filed 12 Jan. 2005, the entire contents of each of which are hereby incorporated by reference.

The present invention forms a part of the technical field relating to the packaging of products in a protected environment.

In particular, the invention relates to a containers sterilising and depyrogenating unit, mainly bottles suitable for being filled with pharmaceutical products, in liquid or powder form, to which the following disclosure makes specific reference without thereby losing in generality.

The object of the invention is to realize a sterilising and depyrogenating unit, the use of which enables optimal, rapid and efficient sterilising and depyrogenating of bottles by selecting at will the four possible alternative modes of combined hot-cold, hot-hot, cold-hot or cold-hot sterilising.

According to the present invention a unit for sterilising and depyrogenating containers is realized of the type comprising conveying means suitable for receiving a plurality of said containers through at least an inlet and supplying the containers in a set direction to a corresponding outlet of the unit; the unit being characterised in that it comprises a sterilising/depyrogenating arrangement defined by at least two sterilising modules arranged consecutively in said direction and communicating through an intermediate passage, and affected by said conveying device; said sterilising modules being activatable independently of one another according to alternative hot sterilising and/or cooling operating modes of the containers.

Figure 1:
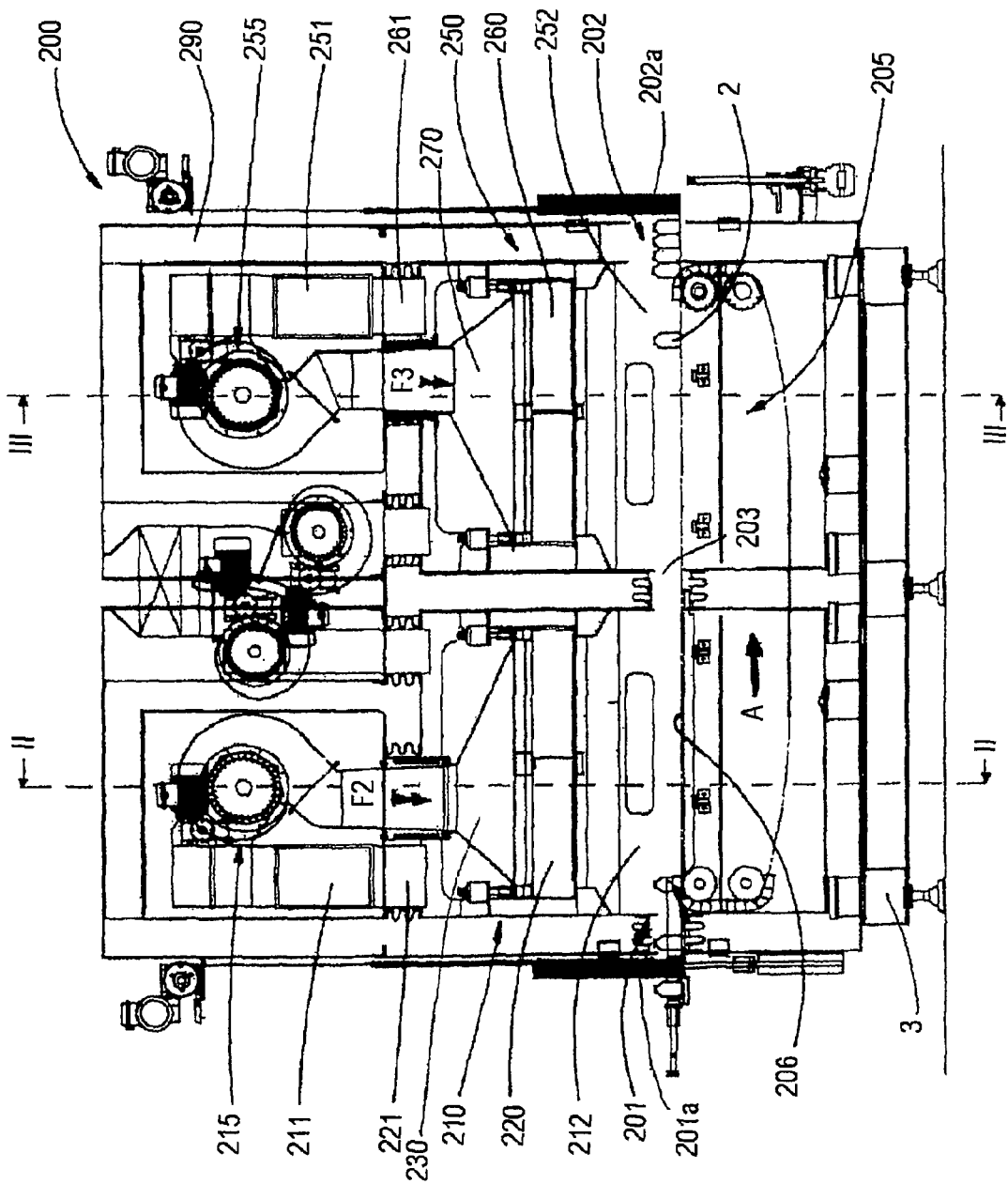
Figure 3:
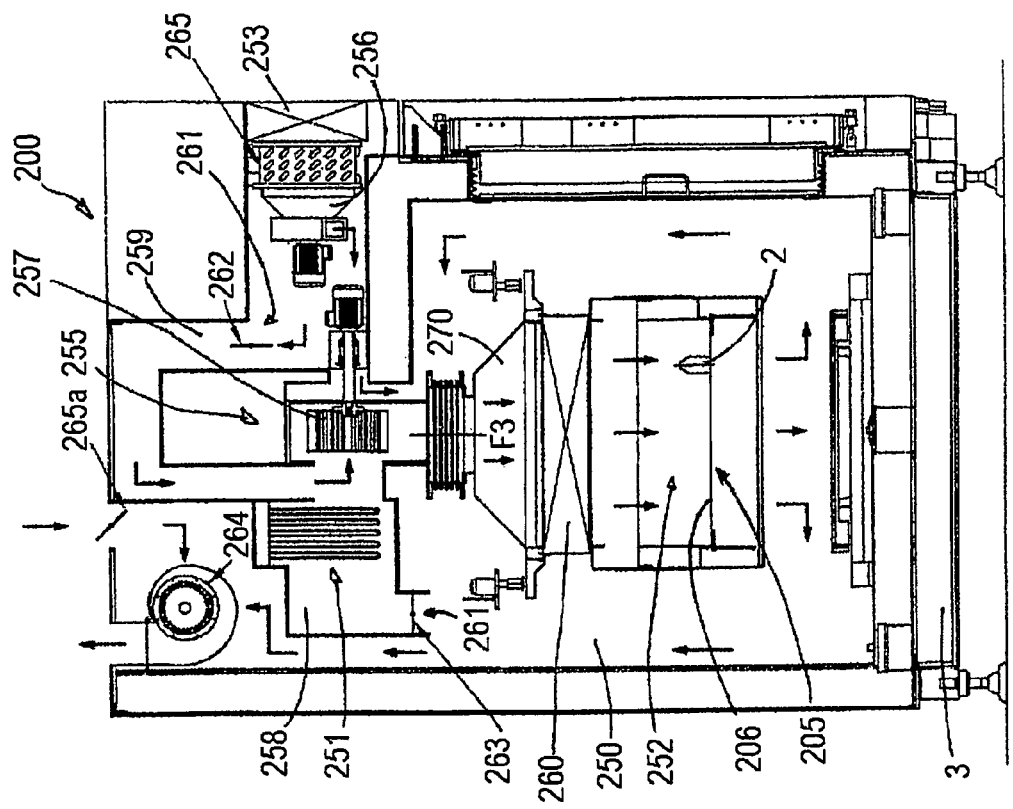
Figure 2:
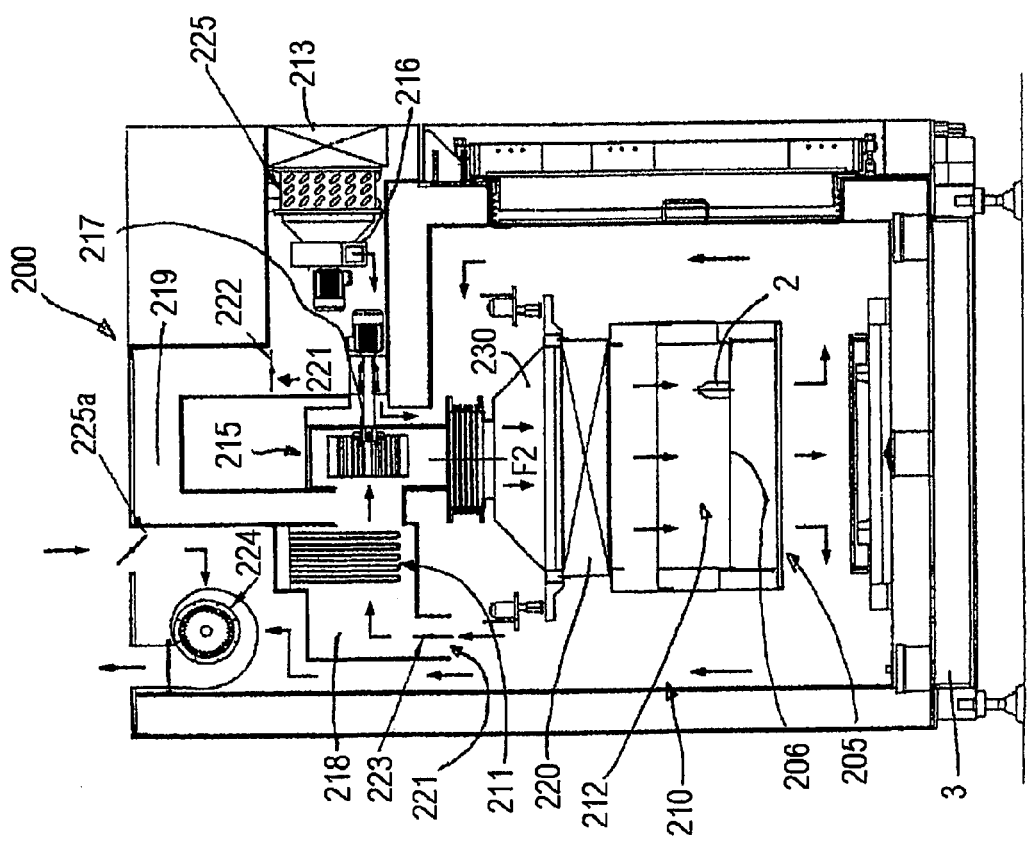

The features of the invention as they will appear from the claims are pointed out in the following detailed disclosure made with reference to the attached drawings, in which:

FIG. 1 illustrates schematically a side view, partially sectioned and with parts removed for clarity, of an embodiment of a unit for sterilising and depyrogenating containers according to the invention in subject; and FIGS. 2 and 3 are two cross-section views respectively according to II-II and according to III-III of the sterilising unit in FIG. 1, in two respective different functional operating positions.

With reference to FIG. 1, 200 indicates overall a unit for sterilising and depyrogenating containers 2, in particular empty bottles 2 suitable for being subsequently filled with liquid or powder material used in the pharmaceutical field.

The unit 200 is defined by a two-stage sterilising arrangement 200 provided with a single base 3, which arrangement 200 comprises a pair of sterilising modules, respectively a first module 210 and a second module 250, arranged consecutively and communicating together by means of an intermediate passage 203.

These modules 210 and 250 of the unit 200 of the present invention are advantageously activatable independently of one another according to operating modes hot and/or cold sterilising the bottles 2.

In other words, by suitably activating in relation to one another the modules 210 and 250, as will be better explained below, it is possible to achieve optimal, rapid and safe sterilising/depyrogenating of the bottles 2 with the following four combined alternative operating modes: hot-cold, hot-hot, cold-cold or lastly, cold-hot.

The entire arrangement 200 is completely enclosed inside a single insulated covering structure 290, intended for preventing significant heat losses to the external environment.

The arrangement 200 furthermore comprises a belt conveyor 205, arranged in the lower part thereof between a loading inlet 201, made in the first sterilising module 210, and an unloading outlet 202, made in the second sterilising module 250.

Still according to what has been illustrated in the attached FIG. 1, the conveyor 205 is intended for supporting an ordered plurality of bottles 2 on an upper branch 206 thereof to convey the bottles 2 in a horizontal advancing direction A inside and through, in sequence, the first module 210 and the second module 250.

The loading inlet 201 and the unloading outlet 202 are provided with corresponding shutters 201a, 202a that are vertically movable suitable for enabling the opening and closing thereof for the passage of bottles 2 respectively entering and exiting the unit 200.

In the first sterilising module 210 a sterilising chamber 212 is obtained, the lower part of which is affected by the aforementioned conveyor 205.

According to what has been better illustrated in FIG. 1, in the upper part of the first module 210 by means of suitable conduits and separating baffles an air flow F2 is realized that is intended for affecting the bottles 2 according to the modes subsequently disclosed to identify two different alternatively selectable heating or cooling paths of the bottles 2.

This flow F2 flows above the conveyor 205 in a hood 230 below which a filtering element 220 is provided that is defined by a HEPA filter the class which is suitable for obtaining the desired degree of air purity.

In the first module 210 a generating device 215 for generating the aforementioned air flow F2 is also provided.

It is important to note that the first 210 and second 250 sterilising modules have a substantially identical structure: thus, similarly to the first module 210, also the second module 250 is suitable for defining a corresponding identical sterilising chamber 252, affected in the lower part thereof by the aforementioned conveyor 205, and is provided with an identical flow generating device 255 for generating an air flow F3 traversing and flowing into a hood 270, with an identical filtering element 260 or HEPA filter.

Therefore, in the embodiment illustrated in FIG. 1, the two modules 210 and 250 are arranged specularly, so that the aforementioned intermediate passage 203 consists of corresponding openings realized in the modules 210, 250 made to match each other.

Further openings made at the opposite ends of the modules 210, 250 respectively form the aforementioned loading inlet 201 and unloading outlet 202 of the present sterilising arrangement 200.

As already mentioned above, both the first module 210 and the second module 250 may operate as both hot or cold sterilisers, as can now be observed respectively in FIG. 2 and in FIG. 3.

According to what has been illustrated in the first part of the aforementioned Figures, FIG. 2, with which for simplicity and clarity it is intended to disclose the first module 210 suitable for operating in hot sterilizing mode, in the first sterilising module 210 the sterilizing chamber 212 is obtained that is affected in the lower part thereof by the aforementioned conveyor 205.

In the upper part of the first module 210 a path is realized for an air flow F3 intended for affecting the bottles 2 according to the modes disclosed below, and comprising two alternatively selectable heating 218 and cooling 219 branches of the bottles 2.

This path leads above the conveyor 205 into the hood 230 below which the aforementioned filtering element 220 or HPA filter are fixed.

Inside the heating branch 218 a heating element 211 is located that is substantially defined by a coil resistor intended for heating the aforementioned air flow F2 up to a preset sterilising/depyrogenating temperature of the bottles 2.

In the first module 210 the aforementioned generating device 215 for generating the aforementioned air flow F2 is also provided.

The generating device 215 comprises an inlet fan 216 arranged at an air intake 213 and suitable for sucking air from the external environment, and a main fan 217, arranged above the aforementioned hood 230 and suitable for conveying to the bottles 2 the air flow F2 through the HEPA filter 220 in a substantially laminar mode.

The first sterilising module 210 further comprises a refrigerating arrangement 225 that is selectively activatable and intended for rapidly cooling the air flow entering the aforementioned first module 210, when the latter is arranged in the cooling operating mode.

At the inlet of the aforementioned heating 218 and cooling 219 branches, flow-commuting members 221 are provided.

These substantially comprise a pair of butterfly commutators 222, 223, that are commutable in push-pull mode between respective open and closed positions to connect or disconnect corresponding heating 218 and cooling 219 branches from the air flow F2 path.

In the upper part of the first module 210 an evacuation fan 224 is provided that is intended for conveying part of the circulating air flow to the external environment.

With this fan 224 a mixing valve 225a is associated, that is arrangeable according to different opening degrees, intended for mixing in suitable proportions air coming from the external environment with the part of the air flow that enters the evacuation fan 224, to lower the temperature of the exiting air.

Similarly to what has been illustrated in FIG. 2, now referring to FIG. 3, with which for simplicity and clarity it is intended to disclose the second module 250 suitable for operating in cold mode, the second module 250 defines the sterilising chamber 252, affected in the lower part thereof by the aforementioned conveyor 205.

In the upper part of the second module 250 a path for an air flow F3 is realized comprising two branches, a heating branch 258 and a cooling branch 259.

This path leads, above the conveyor 205, into the bell 270, below which the aforementioned HEPA filter 260 is fixed.

Inside the heating branch 258 a heating element 251 is arranged, which may be defined by a coil resistor and is intended for heating the air flow up to the aforementioned preset sterilising and depyrogenating temperature of the bottles 2.

In the second module 250 a generating device 255 for generating the aforementioned air flow F3 is also provided.

The generating device 255 comprises an inlet fan 256 arranged at an air intake 253 and suitable for sucking in air from the external environment, and a main fan 257, arranged above the aforementioned hood 270.

A refrigerating arrangement 265 is further present that is selectively activatable and is intended for rapidly cooling the air flow F3 entering the second module 210, when the latter is arranged in the cooling operating mode.

At the inlet of the aforementioned heating 258 and cooling 259 branches flow-commuting members 261 are provided.

These substantially comprise a pair of butterfly switches 262, 263 commutable in push-pull mode as already disclosed previously.

In the upper part of the second module 250 an evacuation fan 264 is provided that is intended for conveying part of the circulating air flow to the external environment.

With this fan 264 a corresponding mixing valve 265a is associated that is arrangeable according to different opening degrees to lower the temperature of the exiting air.

By way of example, the operation of the sterilising and depyrogenating unit 200 for sterilising/depyrogenating the bottles 2 according to a hot-cold sterilising mode is now disclosed (from which it is also possible to deduce the other already aforementioned operating modes of the unit 200, i.e. hot-hot, cold-hot or cold-cold).

The first sterilising module 210 receives a batch of bottles 2, already suitably washed and decontaminated, from the loading inlet 201 on the conveyor 205.

The butterfly commutator 222 at the inlet of the heating branch 218 is taken to the open position whereas the commutator 223 at the inlet of the cooling 219 branch is taken to the closed position.

The refrigerating arrangement 225 is kept inactive and the fans 216, 217 are activated to create the air flow F2 to the bottles 2.

The air is then progressively heated, consequently heating the bottles 2 until the bottles 2 are brought up to the desired sterilising and depyrogenating temperature.

The bottles 2 are kept at this temperature for a preset period, after which the bottles 2 are conveyed from the conveyor 205 to the second module 250, which realizes cooling.

Simultaneously, a new batch of bottles 2 to be sterilised can be loaded into the first sterilising stage 210 through the loading inlet 201.

In the aforementioned second module 250 the butterfly commutator 262 is kept closed, whereas the commutator 263, that inserts the cooling branch 259 into the air flow path, is kept open.

The inlet 256 and main 257 fans are then activated, as well as the refrigerating arrangement 265.

The bottles 2 are then affected by a laminar flow of cold air and are brought up to a temperature that is compatible with the subsequent packaging operations.

The bottles 2 are then conveyed by the conveyor 205 to the unloading outlet 202 and then to a subsequent filling step of the bottles 2 with liquid or powder material.

The two-stage structure of the sterilising unit 200 as disclosed above enables several advantages to be obtained.

First of all, the possibility of having significant flexibility of use in function of different production needs. Further, the identical configuration of the two modules/stages with the possibility for both to carry out sterilising cycles, enables the internal environments of the two modules to be kept sterile always and in all cases.

In fact, performing a sterilising cycle on the bottles also automatically makes the operating environments sterile.

This constitutes a significant advantage compared with known sterilising devices which have to provide different and independent means for carrying out periodic sterilising cycles in the cooling section of the containers.

A further advantage is due to the fact that for the same production volumes the sterilising modules can be realized with smaller dimensions. The construction of a larger number of identical modules that therefore use identical components furthermore enables significant savings in production costs to be made.

It is understood that everything disclosed above has been disclosed purely by way of non-limitative example.

Possible modifications to and variations on the invention are therefore considered to fall within the extent of the protection accorded to this technical solution as disclosed above and claimed below.

The invention claimed is;

1. Unit for sterilising and depyrogenating containers of the type comprising a conveying device suitable for receiving a plurality of said containers through at least an inlet and supplying said containers in a set direction to a corresponding outlet of the unit wherein said unit comprises a sterilising/depyrogenating arrangement defined by at least two sterilising modules, arranged consecutively in said direction and communicating through an intermediate passage, and affected by said conveying device; said sterilising modules being activatable independently of one another according to alternative operating modes for hot sterilising and/or cooling said containers, wherein each of said at least two sterilising modules comprises:

a generating device for generating an air flow, suitable for generating and conveying said air flow along a path to said containers;

a filtering element suitable for filtering said air flow up to a preset degree of purity;

a heating element suitable for heating said air flow and intended for affecting said containers inside a sterilising chamber to take said containers to a preset sterilising and depyrogenating temperature, along a heating branch affected by said heating element;

a refrigerating arrangement suitable for cooling said air flow along a cooling branch affected by said refrigerating arrangement;

a flow commuting member, arranged along said heating branch and a further flow commuting member arranged along said cooling branch;

said flow commuting member and said further flow commuting member being commutable between respective open and closed positions to connect or disconnect said heating branch or said cooling branch from said air flow path such that each of said at least two sterilising modules is selectively and alternatively operatable as a hot steriliser and in a cooling operating mode.

2. Unit according to claim 1, wherein said sterilising/depyrogenating arrangement is completely enclosed inside a single insulated covering structure.

3. Unit according to claim 1, wherein said two sterilising modules are substantially identical to each other; said inlet being provided in a first of said sterilising modules in relation to said direction and said outlet being provided in the second of said sterilising modules; said inlet and outlet being provided with relative corresponding shutters suitable for enabling the opening and closing thereof at the passage of said containers respectively entering and exiting said unit above said conveying device.

4. Unit according to claim 1, wherein said flow-commuting member and said further flow commuting member comprise respective butterfly commutators commutable in push-pull mode between respective open and closed positions.

5. Unit according to claim 1, wherein each of said sterilising modules comprises an evacuation fan suitable for conveying part of said air flow to the external environment; a corresponding mixing valve being associated with said evacuation fan.

6. Unit according to claim 1, wherein the unit is configured to operate in the following alternative operating modes:

hot-cold, wherein the first module operates in the hot sterilising mode and the second module operates in the cooling operating mode;

hot-hot, wherein both of the modules operate in the hot sterilising mode;

cold-cold, wherein both of the modules operate in the cooling operating mode; and cold-hot, wherein the first module operates in the cooling operating mode and the second module operates in the hot sterilising mode.

* * * * *

UNITED STATES PATENT AND TRADEMARK OFFICE
CERTIFICATE OF CORRECTION

PATENT NO. : 7,811,533 B2
APPLICATION NO. : 11/794656
DATED : October 12, 2010
INVENTOR(S) : Claudio Bechini Page 1 of 1

It is certified that error appears in the above-identified patent and that said Letters Patent is hereby corrected as shown below:

Title Page, Item (73) should read

-- (73) Assignee: IMA LIFE S.R.L.
Ozzano Dell'Emilia (BO) (IT) --.

Signed and Sealed this
Fifteenth Day of November, 2011

David J. Kappos
*Director of the United States Patent and Trademark Office*